United States Patent [19]
Rosenthal et al.

[11] Patent Number: 5,516,487
[45] Date of Patent: May 14, 1996

[54] ABSORBENT PAPER FOR LIQUID SAMPLING AND IMPREGNATED PAPER CALIBRATORS AND CONTROLS

[75] Inventors: Murray A. Rosenthal, Copley; Vincent J. Greczanik, Akron; Ronald A. Simkins, Wooster, all of Ohio

[73] Assignee: Isolab, Inc., Norton, Ohio

[21] Appl. No.: 263,580

[22] Filed: Jun. 22, 1994

[51] Int. Cl.⁶ .................................................. G01N 21/84
[52] U.S. Cl. ............................... 422/55; 422/58; 422/61; 436/174
[58] Field of Search ..................... 422/55, 58, 61, 422/99; 436/174; 73/863

[56] References Cited

U.S. PATENT DOCUMENTS 3,346,464  10/1967  Ernst ............................ 422/61 X
5,334,502   8/1994  Sangha .......................... 422/55 X

*Primary Examiner*—Lyle A. Alexander
*Attorney, Agent, or Firm*—Standley & Gilcrest

[57] ABSTRACT

The present invention is an absorbent paper piece having a plurality of samples zones adapted to receive a liquid sample. The paper comprises an absorbent paper piece having a plurality of sample zones, each sample zone having a perforation extending substantially around its perimeter, so as to substantially obstruct the capillary flow of the liquid sample from one of the sample zones having an there sample zone adjacent thereto, to the other sample zone. It is preferred that the absorbent paper piece be provided with barrier perforations interposed between adjacent sample zones, so as to provide a gap between the sample zones as an additional capillary flow barrier. The absorbent paper piece may be adapted to hold any desired sample in liquid form such as laboratory reagents, and biological samples, such as blood samples (here used to include blood, products or components of blood, and blood hemolysate). The blood or blood products may also be arrayed in a series of sample zones for purposes of control and calibration, in accordance with practices known in the art.

23 Claims, 5 Drawing Sheets

5,516,487

ABSORBENT PAPER FOR LIQUID SAMPLING AND IMPREGNATED PAPER CALIBRATORS AND CONTROLS

TECHNICAL FIELD

The present invention includes absorbent paper for containing a liquid sample and blood product impregnated paper calibrators and controls for use in assays for samples collected in this manner.

BACKGROUND ART

In laboratory and clinical settings, it is often necessary to take, contain, transport and store fluid samples, such as blood or blood products, for purposes of analysis.

Liquid sample collection, handling, transport and storage has many problems associated with it including: (1) the risk of container breakage or leakage which causes loss of sample and the danger of infection; (2) sample instability during shipment and storage; (3) refusal of transport carriers to accept liquid biohazardous shipments; (4) collection of more sample than is necessary for testing, to ensure that the blood does not dry out or concentrate in the collection tube. To overcome these problems, some samples are collected on filter paper and dried prior to transport. These samples are mailable and are accepted by all common carriers. Sample stability has been demonstrated for several analytes.

Paper blood collection is currently being used by almost every newborn screening program in the U.S. [Therell 1993]. In order to test newborns for metabolic and genetic disorders, samples are obtained by heel-prick and spotted onto filter paper prior to release of the infant from the hospital or birthing center. To run an assay, a sample disk (typically a 1/8 inch or 1/4 inch circle) is punched out of the larger dried blood spot circle. This method of sample collection not only overcomes the transport and storage problems of liquid samples, but much less sample is collected. This is important because babies have a much smaller blood volume than older children or adults. It is also much easier for the phlebotomist to do a skin prick than a venipuncture on a newborn baby.

Collection of blood on paper has been used for several decades to transport blood for newborn screening. There is a standard protocol used for doing this [NCCLS, see reference 2 below]. There is also a standard paper used to collect blood samples that is universally used [Therell 1993; NCCLS, reference 2 below] in the U.S. Such standard paper is Schleicher and Schuell (Keene, N. H.) grade 903 filter paper. In 1976, Mitchell [see reference 3] described an assay for thyroxine in dried blood spots to detect hypothyroid infants. Travis et al. (1979) evaluated two commercial methods for measuring thyroid hormones in dried blood spots. These commercial methods included reference standards (calibrators) and controls dried on paper. Hearn and Hannon (1982) described an interlaboratory survey in which dried filter spots, made by the Centers for Disease Control (CDC), were assayed by many laboratories. In this article, the authors describe a method for dispensing the blood onto the paper. This procedure entails dispensing blood (100 µL) within 12-mm circles stamped (or printed) onto the filter paper. During the dispensing process, the papers were held in a flat horizontal position by doublestick tape to wooden rails. This was done in order to lift the paper off of the surface and to keep the paper from curling-up (bending) during the drying process. The blood spots papers were dried overnight attached to the wooden rails. Similar surveys were later reported by Spierto et al. [see reference 6] and Slazyak et al. (1988). In the latter, the effects of using printed versus unprinted paper on absorbency is discussed. There may be a loss of absorbency due to the compression of the printed ring during the printing process. Spencer et al. (1993) reported the use of filter paper spot blood collection in screening adult samples for Down Syndrome carriers by measuring chorionic gonadotropin (hCG). They stated that hCG is unstable when stored in liquid blood after several days, and report that filter paper dried blood collection is the method of choice. O'Broin (1993) showed that blood viscosity differences can result in blood volume differences in paper spots due to "spreadability" of the blood during dispensing.

For purposes of convenience, efficiency and the desire to have multiple samples to assure repeatability, it is often the case that a number of sample spot zones are placed in close proximity to one another on a single absorbent paper. One of the difficulties in the use of paper spot sampling is avoiding cross contamination of adjacent sample spot zones. Accordingly, it is desirable to be able to produce a sampling paper that resists sample spreading by capillary action. It is also desirable to produce paper-spotted controls and calibrators, for use with assay techniques using paper spot samplings, which can be prepared while resisting spreading and cross-contamination.

SUMMARY OF THE INVENTION

The invention, in general terms, is an absorbent paper piece having a plurality of sample zones adapted to receive a liquid sample. The paper comprises an absorbent paper piece having a plurality of sample zones, each sample zone being defined by a respective perimeter, and each sample zone having a perforation extending substantially around its respective perimeter, so as to substantially obstruct the capillary flow of the liquid sample from one of the sample zones having an other sample zone adjacent thereto, to the other sample zone. It is preferred that the perforation extend substantially around the sample zone perimeter so as to leave only small portion of the paper bridges the gap, formed by the perforation, between the sample zone and the balance of the paper piece. This has the effect of substantially isolating the sample zone from capillary flow both into and out of the sample zone.

An absorbent paper piece may have, for instance, from 2 to 100 sample zones, but typically will have about 15 to 40 such zones. The zones may be in any geometric array, and the invention is not limited to any particular arrangement(s) of zones. It is however preferred that the zones be arranged in straight arrays for convenient reference, registration and organization. Other arrangements, such as circular or arcuate arrays may be used as appropriate for the desired application.

The invention is not limited to any particular sample zone shape which may be square, circular, oval or ovoid, for example. It is preferred that the sample zones be circular and of sufficient size to accommodate the desired liquid sample volume, to permit the formation of a uniform sample spot.

The perforations used in the present invention may be of any type, but it is preferred that they be a series of elongated cuts to provide relatively large cut lengths around the sample zone perimeter. Where the sample zones are of a shape selected from the group consisting of circles, ovals and ovoids, the sample zone perforation preferably are a series of arcuate cuts.

It is also preferred that the absorbent paper piece be provided with barrier perforations interposed between adjacent sample zones, so as to provide a gap between the sample zones as an additional capillary flow barrier. It is preferred that the barrier perforation be a single cut to provide a complete gap.

For many applications, it will be desirable to use the absorbent paper piece to hold more than one subseries of sample zones, for organizational purposes. For instance, a given paper piece may be provided with 25 zones divided into 5 subseries to hold five sample spots from each of five sources (such as five individuals), or to have each subseries be an array of sample spots each of which hold a different reagent, control substance, or control substance concentration (such as a hemoglobin control), thus giving a total of five reagent/control series. Accordingly, in such situations, the plurality of sample zones is divided into at least two sample zone subseries, with the sample zone subseries separated by a perforation so as to allow each the sample zone subseries to be separated from one another. In many cases, it will be desirable to be able to take uniform punchings from each of the sample zones in a given subseries. For this purpose, it is preferred that where each of the at least two sample zone subseries is contained on a respective sub-part of the absorbent paper piece, each the sub-part of the absorbent paper piece has sufficiently small dimensions to allow a portion of the sub-pan to be punched out of each its the respective sample zone subseries (typically using a standard hole punch). Reducing the size of the paper piece subparts of course gives the advantage of reducing the overall amount of paper used in the paper piece.

The absorbent paper piece may be adapted to hold any desired sample in liquid form such as laboratory reagents, and biological samples, such as blood samples (here used to include blood, products or components of blood, and blood hemolysate). In the case of blood products, it is preferred that the blood sample contain sucrose, preferably in the range of from about 0.5% to about 20% by weight of the blood sample. The blood or blood products may also be arrayed in a series of sample zones for purposes of control and calibration, in accordance with practices known in the art. Control and calibration concentrations and/or ranges of concentration may be selected as desired.

The preferred paper used in accordance with the present invention is an absorbent, pure cotton linter, white, binderless paper.

The paper piece of the present invention may be used, for instance, for the production of biological controls, such as blood controls, such as those used in test kits. In the present invention, calibrator and control blood are dispensed onto a paper piece of the present invention. The paper may be die cut or laser cut, and are cut in such a way, and with due regard to size of the sample zones and the distance between them, so as to: (1) create a uniform circle of blood, (2) prevent blood overlap between adjacent circles of blood, (3) prevent a non-uniform distribution of analyte as a result of improper spreading, and (4) prevent bending or curling of the paper during the drying process without use of an immobilization frame. It is advantageous to dispense calibrator and control paper so that a minimum amount of paper is used. This not only saves paper, but allows easier access to punch samples and reduces the bulk of the packaging needed to store calibrators and controls for use in a kit.

DETAILED DESCRIPTION OF THE PREFERRED EMBODIMENT AND BEST MODE

In accordance with the foregoing summary, the following describes a preferred embodiment of the present invention, which is also considered to be the best mode of the invention.

Figure 1:
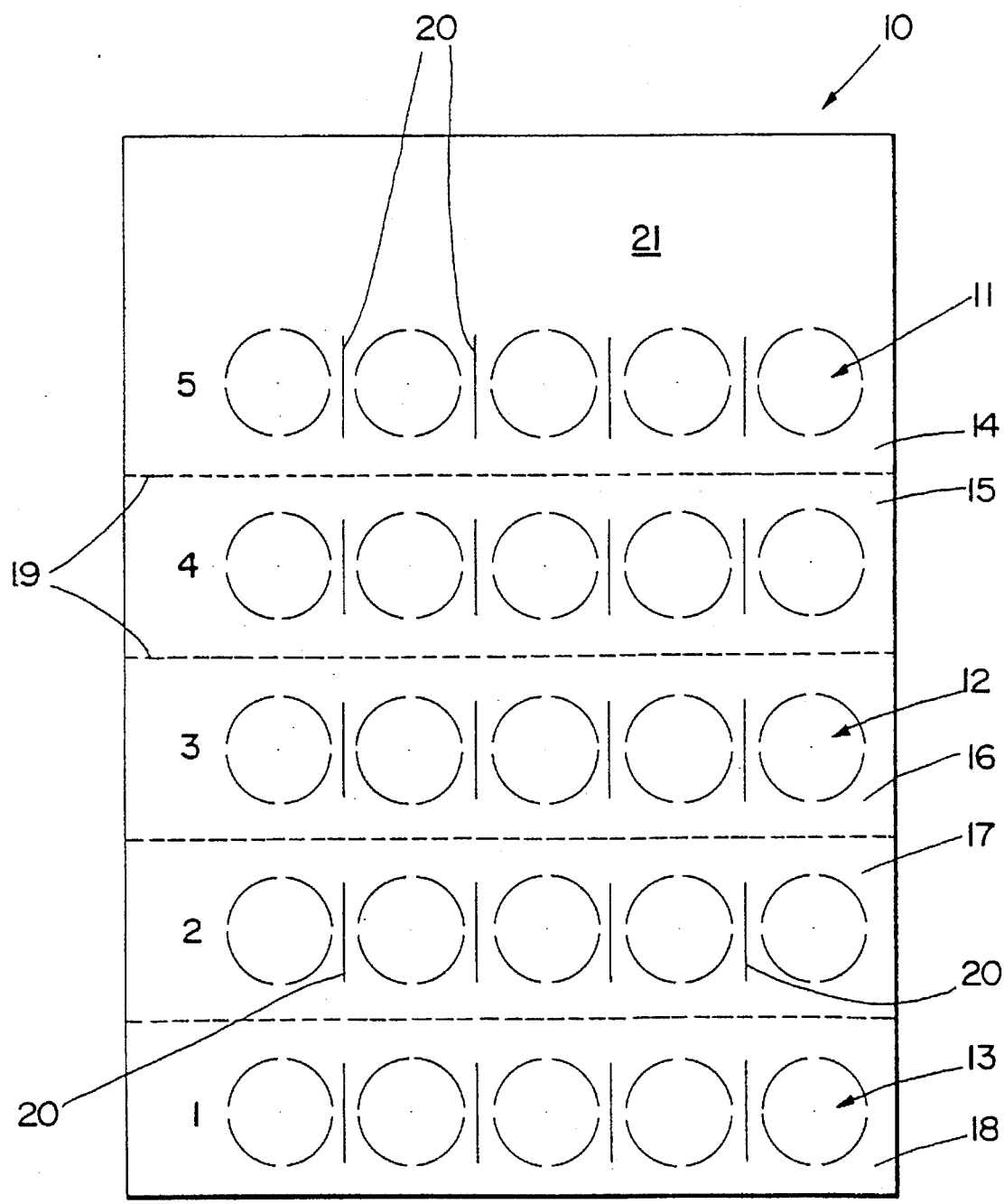
FIG. 1 is a plan view of an absorbent paper sampling device in accordance with one embodiment of the present invention.

An example of the cut pattern is shown in FIG. 1. FIG. 1 shows a paper piece in accordance with the present invention having sample zones for 25 blood spots (15 mm) on a single 158×114 mm card.

FIG. 1 shows an absorbent paper piece 10 perforated in accordance with the present invention. FIG. 1 shows paper card 10 provided with twenty-five (25) sample zones (e.g., 11, 12 and 13) in five series (numbered 1–5) of five sample zones each; each series being disposed on five subparts 14 through 18. Subparts 14 through 18 are separated by perforations 19. Adjacent sample zones are separated by a small paper area that is supplied with barrier slits 20. Card 10 may also be provided with identifying indicia. Additional space (e.g., area 21 ) may be provided along one side or along the top or bottom to apply a label. Disks are generally punched starting at series row 1. After series row 1 has been punched, corresponding subpart 18 can be torn off at the respective perforation in order for a standard hole puncher to be able to reach all of the spots on series row 2.

The perforations 19 and barrier slits 20 between spots function to prevent blood from flowing between the spots. Uniform circles are die-cut or laser cut into the paper to insure that: (1) blood will not flow between the circles, (2) a product results which is uniform in appearance, (3) cards with spots that do not completely fill all circles can be easily noticed by visual inspection and can be discarded. The paper is not completely cut around the perimeter of each circular sample zone; rather there are, in this embodiment, four small uncut areas in the sample zone circumference that function to hold the circular sample zone to the card.

The present also includes a method of stabilizing analytes in the spot calibrator and controls. Specifically, the experimental results shown here indicate that galactose (GAL), used to screen for galactosemia, is unstable in dried blood spots. Galactose levels tend to drop after long periods of storage, especially at elevated temperatures. In the preferred embodiment in the area of galactose measurement, antibiotics and sucrose have been added to improve stability. Also added to the blood spots in the examples is a phenylalanine (PHE) analyte, used to screen for phenylketonuria.

Figure 5:
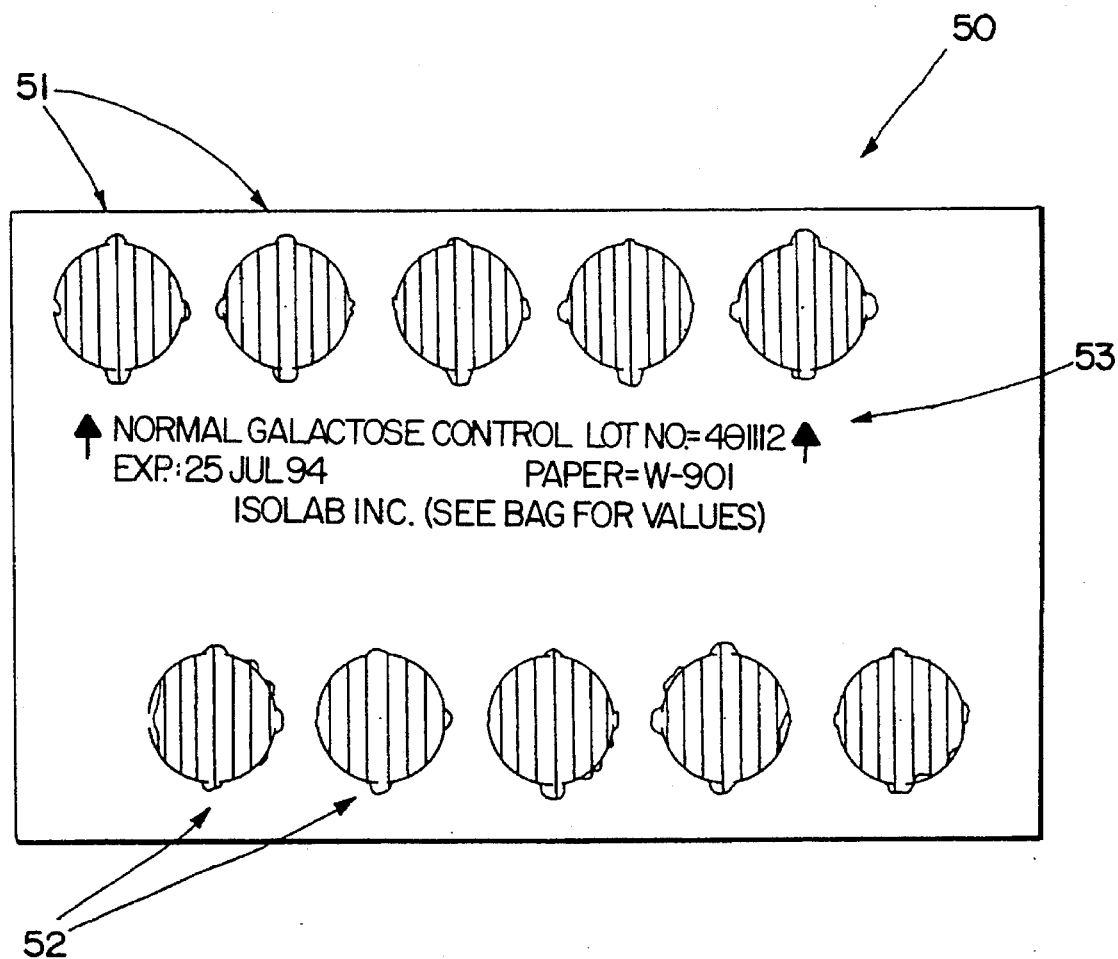
FIG. 5 is a plan view of an absorbent paper sampling device in accordance with one embodiment of the present invention, showing the appearance of liquid samples applied thereto.

FIG. 5 shows an absorbent paper piece perforated in accordance with the present invention and adapted for use as a galactose control for normal and elevated galactose levels, using five sample zones for each of the two levels. FIG. 5 shows paper card 50 provided with five normal galactose level zones 51 and five elevated galactose level zones 52. Identifying indicia 53 may also be included on the paper card.

Figure 6:
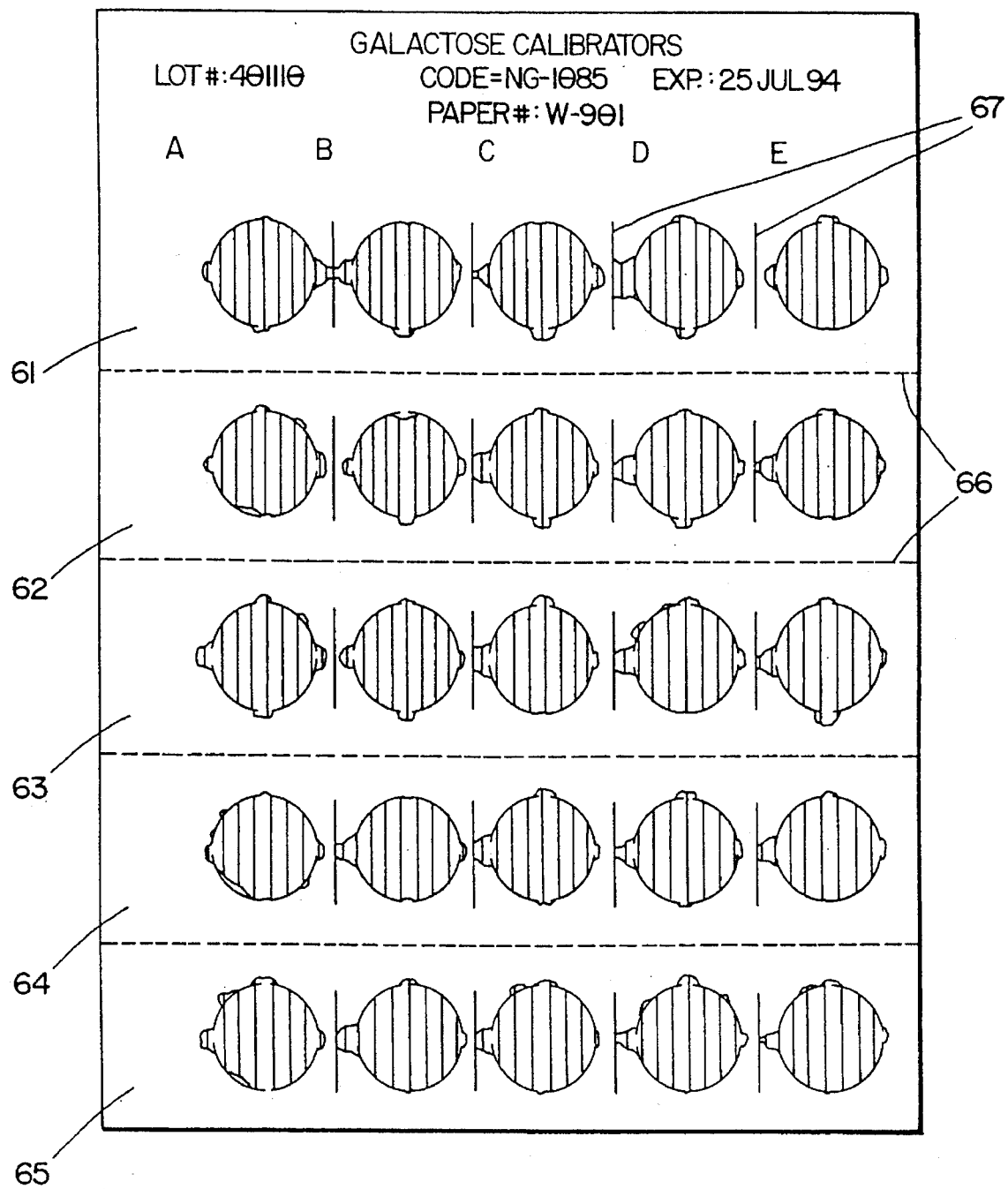
FIG. 6 is a plan view of an absorbent paper sampling device in accordance with yet another embodiment of the present invention, showing the appearance of liquid samples applied thereto.

FIG. 6 shows an absorbent paper piece perforated in accordance with the present invention and adapted for use as galactose calibrators. Card 60 contains five series of five sample zones each; each series being disposed on five subparts 61 through 65 and containing five sample zones A–E. Subparts 61 through 65 are separated by perforations 66. Adjacent sample zones are separated by a small paper area that is supplied with barrier Slit 67. Card 60 may also be provided with identifying indicia 68.

Both FIGS. 5 and 6 are shown with liquid samples applied to all of the sample zones, which appear as dark stains. FIGS. 5 and 6 demonstrate how the arrangement of the sample zones, the perforation around their perimeters, and the barrier slit prevent the cross-contamination of adjacent sample zones.

The best mode for carrying out the invention is shown in Example 1.

EXAMPLES

Example 1

Paper cards were laser-cut from Schleicher and Schuell grade 903 filter paper in a model 1720C laser cutter from Universal Laser Systems, Inc. (Scottsdale, Ariz.) using the pattern indicated in the FIG. 1. Human whole blood (citrate-phosphate-dextrose anticoagulated) was washed three times with isotonic saline. The packed cells were frozen, thawed and adjusted to 17 g/dL hemoglobin content by dilution with water. The following antibiotics were added: Proclin 300 (0.5 mL/L, Supelco, Bellefonte, Pa.), gentamicin sulfate (0.1 g/L, Sigma, St. Louis, Mo.) and chloramphenicol (0.02 g/L, Sigma). Sucrose (60 g/L, Sigma) was also added. After gentle mixing for 15 minutes at room temperature, the blood was apportioned into five equal volumes. A stock solution containing 1.00 g/dL of phenylalanine (Sigma) and 2.00 g/dL (Sigma) of galactose was prepared. The following volumes of GAL/PHE stock was added to each of the five portions of blood:

| CALIBRATOR | STOCK, mL/L OF BLOOD | GAL mg/dL | PHE mg/dL |
| --- | --- | --- | --- |
| A | 0 | 0 | 0 |
| B | 2.5 | 5 | 2.5 |
| C | 5.0 | 10 | 5 |
| D | 7.5 | 15 | 7.5 |
| E | 10.0 | 20 | 10 |

The blood was mixed for five minutes and during dispensing. The paper cards were laid out on a plastic surface (saran film). Using a pipette, 75 μL of blood was dispensed onto the center of each of the 5 circles in the corresponding column on each card. The spots were dried in place for four hours. They were then placed in a 37° C. oven overnight. The cards were placed in plastic bags containing a desiccant pouch and stored refrigerated. This procedure resulted in calibrator cards containing 5 different levels of two analytes. The cards were not noticeably bent or bowed. There was no cross contamination of the blood between circles. Each circle was completely filled with blood. During dispensing, we noted that the paper absorbed the sample until the liquid blood reached the circumference cut.

Example 2

Controls were prepared as in Example 1 on both cut and uncut Schleicher and Schuell grade 903 paper. Low spot controls had 3 and 6 mg/dL, respectively of PHE and GAL added to the blood prior to spotting. High spots had 6 and 12 mg/dL, respectively of PHE and GAL added to the blood prior to spotting. The blood was dispensed much further apart on the uncut cards so that cross-contamination did not occur. After dispensing, the uncut cards were much more noticeably bent or bowed than the cut cards.

Figure 2:
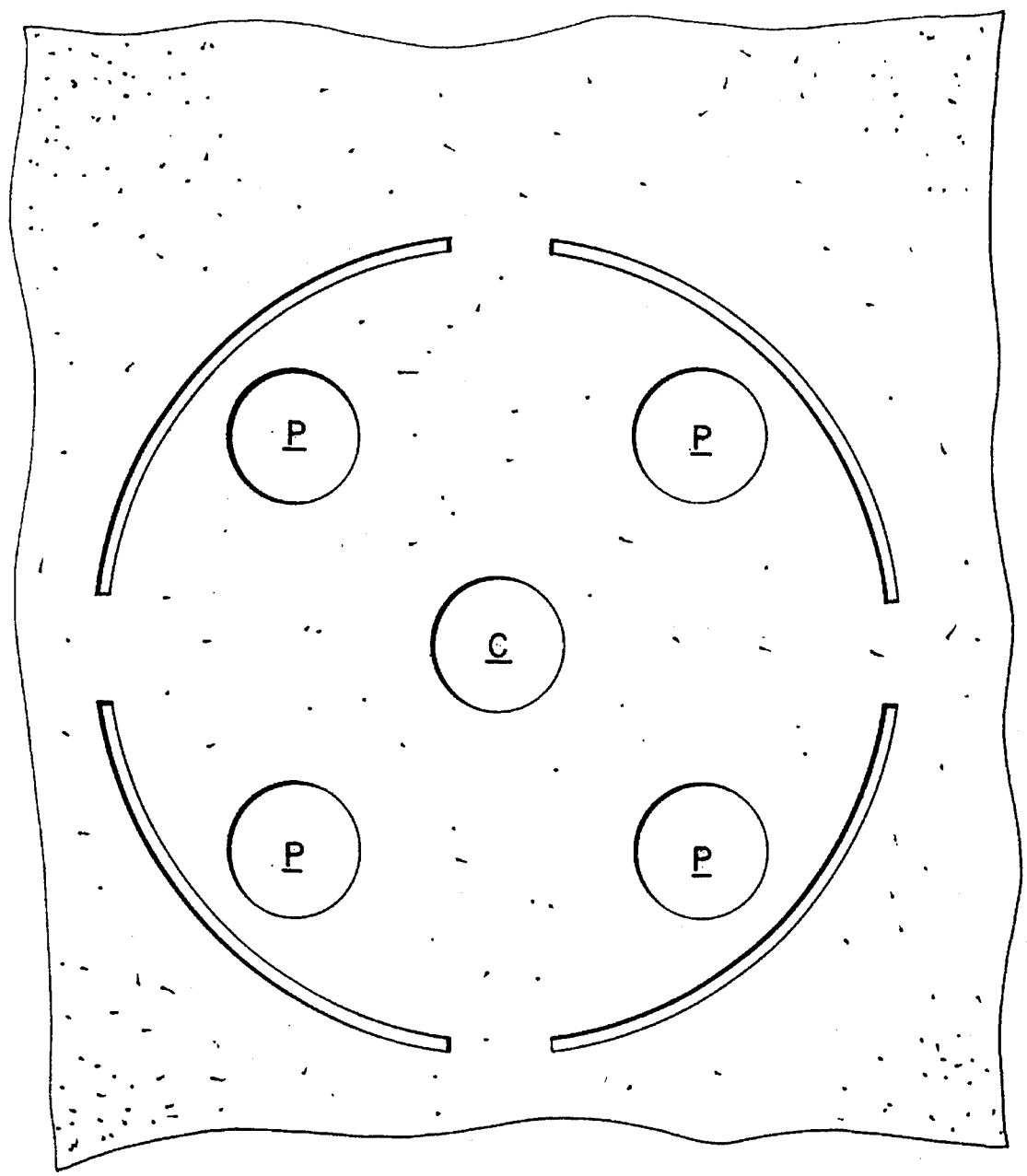
FIG. 2 is a plan view of a portion of a perforated absorbent paper sampling device in accordance with one embodiment of the present invention such as shown in FIG. 1; and showing a single sample zone with several holes punched therein for testing purposes.

PKU Kit components (commercially available from Isolab, Inc. of Akron, Ohio) were used to assay for PHE in blood spots and Galactosemia (Galactose oxidase-based) Kit components (also commercially available from Isolab, Inc. of Akron, Ohio) were used to assay for GAL in the same spots. For the experiment, ⅛" disks were punched from the periphery (P) and center (C) of four cut or four uncut blood spots as shown in FIG. 2. GAL and PHE were extracted from the disks. The assays were performed as described in the instructions for each kit.

Figure 3:
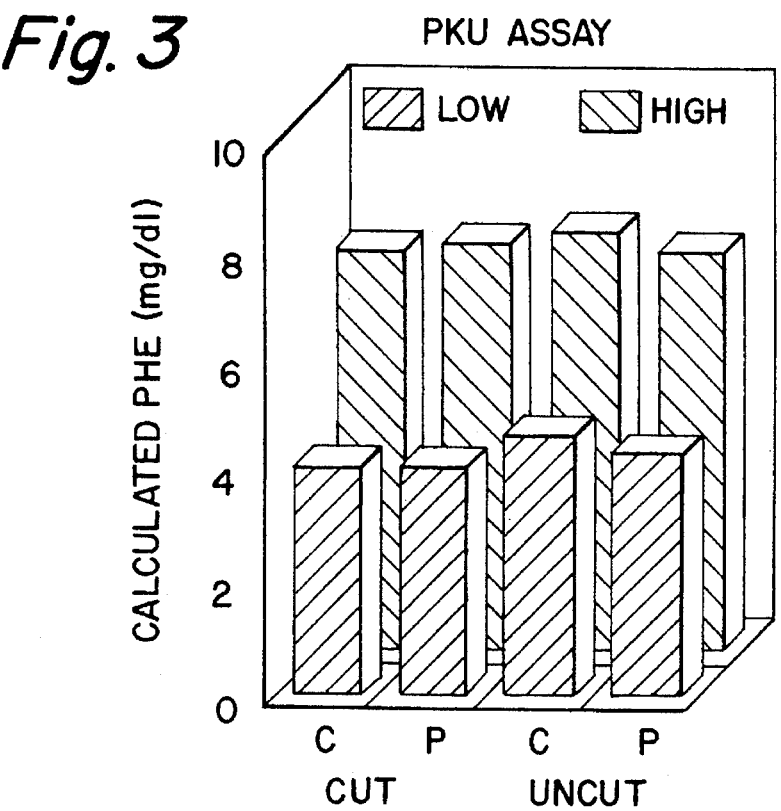
FIG. 3 is a three-dimensional bar graph of results from a phenylalanine assay.
Figure 4:
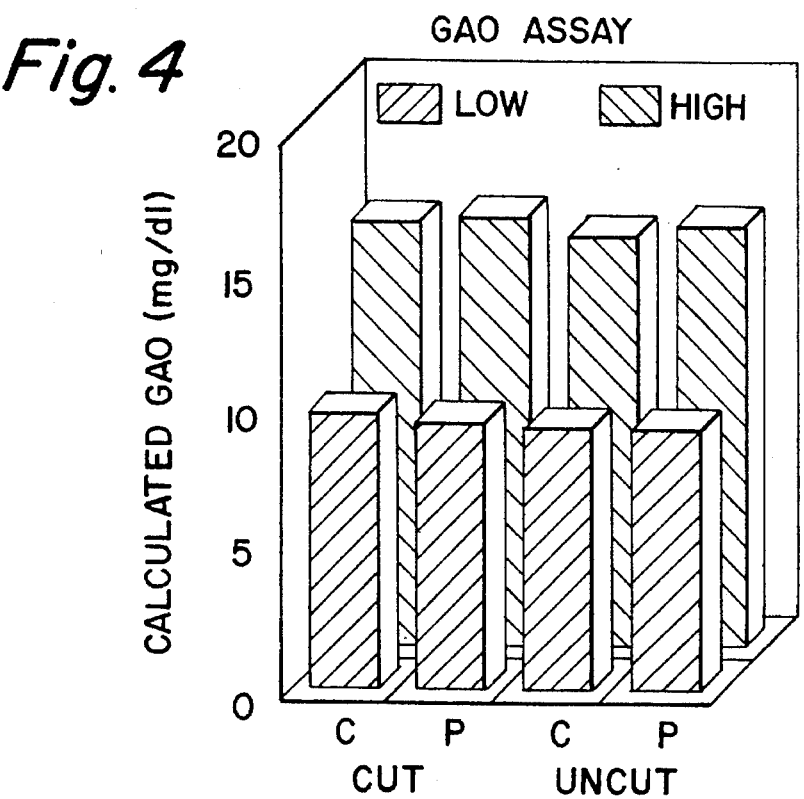
FIG. 4 is a three-dimensional bar graph of results from a galactose assay.

The results of the assays are summarized in the FIGS. 3 and 4. Each bar represents the mean of 4 center or 16 peripheral disks punch from either cut or uncut blood spots. A t-test (assuming equal variance) indicated that there were no statistical differences between disks cut from the periphery and center of the spots. Thus, the distribution of galactose and phenylalanine in blood spotted onto cut and uncut Schleicher & Schuell 903 paper appears to be uniform in these assays.

Example 3

The stability of calibrators made as in Example 1 was checked with and without the addition of sucrose. The blood made without sucrose spread much more quickly than the sucrose-containing blood across the card. However, the blood was still contained inside the cut circle. Thus the sucrose functioned to increase the thickness of the blood so that it spread at a rate closer to that of regular whole blood. To check for high temperature shipping stability and as indication of long term refrigerated stability (accelerated aging), the calibrators were incubated at 37° C. in their storage bags (with desiccant) for eight days. The galactose levels of two refrigerated samples, run using standard curves from both the refrigerated and the 37° C. incubated calibrators, were checked as in Example 2. The results are expressed as the percentage of change of the 37° C. incubated calibrators versus the refrigerated calibrators:

| Parameter | With Sucrose | No Sucrose |
| --- | --- | --- |
| Calibrator Slope | −18.8% | −16% |
| Calibrator Intercept | 0% | −8.6% |
| Sample A (4 mg/dL GAL) | +21% | +96% |
| Sample B (20 mg/dL GAL) | +23% | +28% |

These results show that sucrose greatly increased the stability of the calibrators during heat stress. The slopes of calibrator curves with and without sucrose were reduced by the heat stress. However, the intercept of the calibrator curve made without sucrose was greatly reduced causing a marked increase in the assayed value of the samples compared to the sucrose standard curve.

The following publications are hereby incorporated herein by reference:
1. Therrell, B. L., ed., *Laboratory Methods for Neonatal Screening*, American Public Health Association, Washington D.C. (1993).
2. National Committee for Clinical Laboratory Standards (NCCLS). *Blood Collection on Filter Paper for Neonatal Screening Programs; Approved Standard*. NCCLS Publication LA4-A2. Villinova, Pa.: NCCLS (1988).
3. Mitchell, M. L., *Improved Thyroxine Radioimmunoassay for Filter Paper Discs Saturated with Dried Blood*. Clin. Chem. 22:1912 (1976).
4. Travis, J. C., Dungy, C. I., Huxtable, R. F., Valenta, L. J., *Methods of Quality Control and Clinical Evaluation of a Commercial Thyroxine and Thyrotropin Assay for Use in Neonates*. Clin. Chem. 25:735 (1979).
5. Hearn, T. L. and Hannon, W. H., *Interlaboratory Surveys of the Quantitation of Thyroxin and Thyrotropin (Thyroid Stimulating Hormone) in Dried Blood Spot Specimens*. Clin. Chem. 28:2022 (1982).
6. Spierto, F. W., Hearn, T. L., Gardner, F. H., Harmon, W. H., *Phenylalanine Analyses of Blood-Spot Control Material: Preparation of Samples and Evaluation of Interlaboratory Performance*.
7. Slazyk, W. E., Phillips, D. L., Therrell, B. L.; Harmon, W. H., *Effect of Lot-to-Lot Variability in Filter Paper on the Quantification of Thyroxin, Thyrotropin, and Phenylalanine in Dried-Blood Specimens*. Clin. Chem. 34:53 (1988).
8. Spencer, K., Marci, J. N., Carpenter, P., Anderson, R., Krantz, D. A., *Stability of Intact Chorionic Gonadotropin (hCG) in Serum, Liquid Whole Blood and Dried Whole-Blood Filter-Paper Spots: Impact on Screening Down Syndrome by Measurement of Free β-hCG Subunit*. Clin. Chem. 39:1064 (1993).
9. O'Broin, S., *Influence of Hematocrit on Quantitative Analysis of "Blood Spots" on Filter Paper*. Clin. Chem. 39:1354 (1993).

In view of the foregoing disclosure or through practice of the present invention, it may be possible to practice the invention through modification and substitution of components and process steps, without departing from the spirit of the invention as reflected in the appended claims.

What is claimed is:

1. An absorbent paper piece having a plurality of sample zones adapted to receive a liquid sample, said paper piece comprising:

an absorbent paper piece having a plurality of sample zones, each said sample zone defined by a respective perimeter, and each said sample zone having a perforation, said perforation comprising a series of elongated cuts, each of said cuts block capillary flow across said gap, extending substantially around said perimeter, so as to substantially obstruct the capillary flow of said liquid sample from one of said sample zones having an other sample zone adjacent thereto, to said other sample zone.

2. An absorbent paper piece according to claim 1 wherein said absorbent paper piece comprises a pure cotton linter, white, binderless paper.

3. An absorbent paper piece according to claim 1 wherein said plurality of sample zones is divided into at least two sample zone subseries, said at least two sample zone subseries separated by a perforation so as to allow each said sample zone subseries to be separated from each other.

4. An absorbent paper piece according to claim 1 wherein said plurality of sample zones is divided into at least two sample zone subseries, said at least two sample zone subseries separated by a perforation so as to allow each said sample zone subseries to be separated from each other, and wherein each of said at least two sample zone subseries is contained on a respective sub-part of said absorbent paper piece, each said sub-part of said absorbent paper piece having sufficiently small dimensions to allow a portion of said subpart to be punched out of each its said respective sample zone subseries.

5. An absorbent paper piece according to claim 1 wherein said plurality of sample zones comprises from 2 to 100 sample zones.

6. An absorbent paper piece according to claim 5 wherein said absorbent paper piece comprises a pure cotton linter, white, binderless paper.

7. An absorbent paper piece according to claim 5 wherein said plurality of sample zones is divided into at least two sample zone subseries, said at least two sample zone subseries separated by a perforation so as to allow each said sample zone subseries to be separated from each other.

8. An absorbent paper piece according to claim 5 wherein said plurality of sample zones is divided into at least two sample zone subseries, said at least two sample zone subseries separated by a perforation so as to allow each said sample zone subseries to be separated from each other, and wherein each of said at least two sample zone subseries is contained on a respective sub-part of said absorbent paper piece, each said sub-part of said absorbent paper piece having sufficiently small dimensions to allow a portion of said sub-part to be punched out of each its said respective sample zone subseries.

9. An absorbent paper piece according to claim 1 wherein said sample zones are of a shape selected from the group consisting of circles, ovals and ovoids, and wherein said sample zone perforation comprises a series of arcuate cuts.

10. An absorbent paper piece according to claim 9 Wherein said absorbent paper piece comprises a pure cotton linter, white, binderless paper.

11. An absorbent paper piece according to claim 9 wherein said plurality of sample zones is divided into at least two sample zone subseries, said at least two sample zone subseries separated by a perforation so as to allow each said sample zone subseries to be separated from each other.

12. An absorbent paper piece according to claim 9 wherein said plurality of sample zones is divided into at least two sample zone subseries, said at least two sample zone subseries separated by a perforation so as to allow each said sample zone subseries to be separated from each other, and wherein each of said at least two sample zone subseries is contained on a respective sub-part of said absorbent paper piece, each said sub-part of said absorbent paper piece having sufficiently small dimensions to allow a portion of said sub-part to be punched out of each its said respective sample zone subseries.

13. An absorbent paper piece according to claim 1 wherein said absorbent paper additionally comprises barrier perforations interposed between adjacent sample zones.

14. An absorbent paper piece according to claim 13 wherein said absorbent paper piece comprises a pure cotton linter, white, binderless paper.

15. An absorbent paper piece according to claim 13 wherein said plurality of sample zones is divided into at least two sample zone subseries, said at least two sample zone subseries separated by a perforation so as to allow each said sample zone subseries to be separated from each other.

16. An absorbent paper piece according to claim 13 wherein said plurality of sample zones is divided into at least two sample zone subseries, said at least two sample zone subseries separated by a perforation so as to allow each said sample zone subseries to be separated from each other, and wherein each of said at least two sample zone subseries is contained on a respective sub-part of said absorbent paper piece, each said sub-part of said absorbent paper piece having sufficiently small dimensions to allow a portion of said sub-part to be punched out of each its said respective sample zone subseries.

17. An absorbent paper piece according to claim 13 wherein said barrier perforations comprise a single elongated cut.

18. An absorbent paper piece according to claim 17 wherein said absorbent paper piece comprises a pure cotton linter, white, binderless paper.

19. An absorbent paper piece according to claim 17 wherein said plurality of sample zones is divided into at least two sample zone subseries, said at least two sample zone subseries separated by a perforation so as to allow each said sample zone subseries to be separated from each other.

20. An absorbent paper piece according to either of claim 17 wherein said plurality of sample zones is divided into at least two sample zone subseries, said at least two sample zone subseries separated by a perforation so as to allow each said sample zone subseries to be separated from each other, and wherein each of said at least two sample zone subseries is contained on a respective sub-part of said absorbent paper piece, each said sub-part of said absorbent paper piece having sufficiently small dimensions to allow a portion of said sub-part to be punched out of each its said respective sample zone subseries.

21. An absorbent paper piece having a plurality of samples zones adapted to receive a blood product sample, said paper comprising:

an absorbent paper piece having a plurality of sample zones, each said sample zone defined by a respective perimeter, and each said sample zone having a perforation extending substantially around its said respective perimeter, so as to substantially obstruct the capillary flow of said blood sample from one of said sample zones having an other sample zone adjacent thereto, to said other sample zone; at least one of said sample zones containing said blood product sample.

22. An absorbent paper piece according to claim 21 wherein said blood product sample contains sucrose.

23. An absorbent paper piece according to either of claim 22 wherein said blood sample contains sucrose present in an amount in the range of from about 0.5% to about 20% by weight of said blood product sample.

* * * * *

UNITED STATES PATENT AND TRADEMARK OFFICE
CERTIFICATE OF CORRECTION

PATENT NO. : 5,516,487
DATED : May 14, 1996
INVENTOR(S) : Murray A. Rosenthal, et al.

It is certified that error appears in the above-identified patent and that said Letters Patent is hereby corrected as shown below:

In the abstract, line 7, "an there" and replace with the word --another--.

In column 4, line 5, after the word "purposes;" please delete the word "and".

In column 4, line 44, please delete the word "tom" and replace it with -- torn--.

In column 7, line 56, after the word "cuts" please add --forming a gap adapted to completely--.

In column 7, line 57, after the word "around" please add --its--.

In column 7, line 57, after the word "said" please add --respective--.

In column 9, line 25, please delete the words "either of".

In column 10, line 23, please delete the words "either of".

Signed and Sealed this

Twelfth Day of November, 1996

Attest:

BRUCE LEHMAN

Attesting Officer           Commissioner of Patents and Trademarks

UNITED STATES PATENT AND TRADEMARK OFFICE
CERTIFICATE OF CORRECTION

PATENT NO. : 5,516,487

DATED : May 14, 1996

INVENTOR(S) : Murray A. Rosenthal, et al

It is certified that error appears in the above-identified patent and that said Letters Patent is hereby corrected as shown below:

In the abstract, line 7, delete "an there" and replace with the word --another--.

In column 4, line 5, after the word "purposes;" please delete the word "and".

In column 4, line 44, please delete the word "tom" and replace it with --torn--.

In column 7, line 56, after the word "cuts" please add --forming a gap adapted to completely--.

In column 7, line 57, after the word "around" please add --its--.

In column 7, line 57, after the word "said" please add --respective--.

In column 9, line 25, please delete the words "either of".

In column 10, line 23, please delete the words "either of".

This certificate supersedes Certificate of Correction issued November 12, 1996.

Signed and Sealed this

Twenty-fifth Day of March, 1997

*Attest:*

BRUCE LEHMAN

*Attesting Officer*   *Commissioner of Patents and Trademarks*